United States Patent [19]

Gilmour et al.

[11] 4,246,021
[45] Jan. 20, 1981

[54] IMIDAZOLE DERIVATIVES

[75] Inventors: James Gilmour, Dagenham; Leslie R. Hatton, Harold Wood; Edgar W. Parnell, Emerson Park; Dennis Warburton, Brentwood; William G. Leeds, London, all of England

[73] Assignee: May & Baker Limited, Essex, England

[21] Appl. No.: 68,681

[22] Filed: Aug. 22, 1979

[30] Foreign Application Priority Data

Aug. 25, 1978 [GB] United Kingdom ............... 34671/78

[51] Int. Cl.$^3$ ..................... A01N 43/50; C07D 233/60
[52] U.S. Cl. .......................................... 71/92; 548/343
[58] Field of Search ............................ 548/343; 71/92

[56] References Cited

FOREIGN PATENT DOCUMENTS 2809022  9/1978  Fed. Rep. of Germany ........... 548/343

OTHER PUBLICATIONS

Khromov-Borisov et al, J. of Org. Chem. (USSR), vol. 9, pp. 2416–2417 (1973).

*Primary Examiner*—Paul M. Coughlan, Jr.
*Attorney, Agent, or Firm*—Stevens, Davis, Miller & Mosher

[57] ABSTRACT

The invention provides new imidazole derivatives of the general formula:

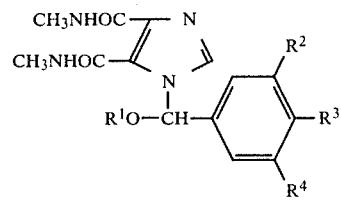

wherein $R^1$ represents a methyl or ethyl group, $R^2$, $R^3$ and $R^4$, which may be the same or different, each represent a hydrogen or halogen atom or an alkyl or alkoxy group which may optionally be substituted by one or more fluorine atoms, and $R^2$, $R^3$ and $R^4$ do not all represent hydrogen atoms, which possess useful herbicidal properties.

30 Claims, No Drawings

IMIDAZOLE DERIVATIVES

DESCRIPTION

This invention relates to new imidazole derivatives, processes for their preparation, herbicidal compositions which contain them, and their use as herbicides.

As a result of research and experimentation, it has been found that the new imidazole derivatives of the general formula:

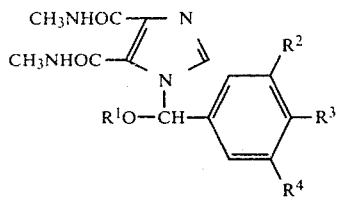

wherein $R^1$ represents an ethyl or, preferably, a methyl group and $R^2$, $R^3$ and $R^4$, which may be the same or different, each represent a hydrogen or halogen (i.e. fluorine, chlorine, bromine or iodine, preferably chlorine or bromine) atom or an alkyl or alkoxy group which may optionally be substituted by one or more fluorine atoms, for example a trifluoromethoxy, 1,1,2,2-tetrafluoroethoxy or, preferably, a trifluoromethyl group, and $R^2$, $R^3$ and $R^4$ do not all represent hydrogen atoms, possess useful herbicidal activity.

Compounds of general formula I wherein one of the symbols $R^2$, $R^3$ and $R^4$ represents a hydrogen atom and the other two symbols and $R^1$ are as hereinbefore defined are preferred.

Especially preferred compounds of general formula I are those wherein $R^1$ is as hereinbefore defined, $R^2$ and $R^3$, which may be the same or different, each represent a hydrogen or halogen atom or an alkyl group which may optionally be substituted by one or more fluorine atoms and $R^2$ and $R^3$ do not both represent hydrogen atoms, and $R^4$ represents a hydrogen or halogen atom.

Compounds of general formula I wherein $R^1$ is as hereinbefore defined, $R^2$ and $R^3$ each represent a halogen atom or $R^2$ represents a hydrogen atom and $R^3$ represents a halogen atom or an alkyl group which may optionally be substituted by one or more fluorine atoms, and $R^4$ represents a hydrogen atom are more especially preferred.

Alkyl groups and the alkyl moieties of alkoxy groups represented by the symbols $R^2$, $R^3$ and $R^4$ may be straight- or branched-chain and contain from 1 to 6 carbon atoms.

As will be apparent to those skilled in the art, compounds of general formula I may exist in optically isomeric, i.e. stereoisomeric forms. The present invention comprises all isomeric forms of general formula I and mixtures, including racemic mixtures, thereof.

Accordingly, a feature of the present invention is a method for controlling the growth of weeds (i.e. undesired vegetation) at a locus which comprises applying to the locus a herbicidally effective amount of at least one imidazole derivative of general formula I. For this purpose, the imidazole derivatives are normally used in the form of herbicidal compositions (i.e. in association with compatible diluents or carriers suitable for use in herbicidal compositions), for example as hereinafter described.

The compounds of general formula I show herbicidal activity against dicotyledonous (i.e. broad-leafed) weeds by pre- and/or, more especially, post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil. For example, the compounds of general formula I may be used to control, more especially by post-emergence application, the growth of annual broad-leafed weeds, for example, *Abutilon theophrasti, Amsinckia intermedia, Anthemis arvensis,* pigweeds (*Amaranthus* spp., e.g. *Amaranthus retroflexus*), *Anoda cristata,* Acanthospermum spp., e.g. *Acanthospermum hispidum, Bidens pilosa,* fat hen (*Chenopodium* spp., e.g. *Chenopodium album*), *Chrysanthemum segetum, Datura stramonium, Descurainea sophia, Emex australis, Galeopsis tetrahit,* Ipomoea spp., e.g. *Ipomoea purpurea,* Lamium spp, e.g. *Lamium purpureum, Merremia aegyptea, Papaver rhoeas,* Physalis spp., e.g. *Physalis lanceifolia, Sida spinosa, Sida rhombifolia,* Sinapis spp., e.g. *Sinapis arvensis, Stellaria media,* Solanum spp., e.g. *Solanum nigrum, Urtica urens,* Veronica spp, e.g. *Veronica persica* and *Xanthium strumarium.*

The amounts of compounds of general formula I applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantially permanent damage to the crop. In general, taking these factors into account, application rates between 0.25 kg and 20 kg of active material per hectare give good results. However, it is to be understood that higher or lower application rates may be used, depending upon the particular problem of weed control encountered.

The compounds of general formula I may be used to control selectively the growth of weeds, for example to control the growth of those species hereinbefore mentioned, by pre- or, preferably, post-emergence application in a directional or non-directional fashion, e.g. by directional or non-directional spraying, to a locus of weed infestation which is an area used, or to be used, for growing crops, for example graminaceous crops, e.g. wheat, barley, oats, rye, maize, rice and sorghum, soya beans, field and dwarf beans, peas, sugar beet, fodder beet and red beet, cotton, peanuts, potatoes, flax, onions, carrots, herbage seed crops, oilseed rape and pasture, before or after sowing of the crop or before or after emergence of the crop. For the selective control of weeds at a locus of weed infestation which is an area used, or to be used, for the growing of crops, e.g. the crops hereinbefore mentioned, application rates between 0.25 kg and 8.0 kg of active material per hectare are particularly suitable.

More particularly, the compounds of general formula I, especially 1-(4-chloro-α-methoxybenzyl)-N,N'-dimethylimidazole-4,5-dicarboxamide, 1-(3-chloro-α-methoxybenzyl)-N,N'-dimethylimidazole-4,5-dicarboxamide, N,N'-dimethyl-1-(α-methoxy-3-trifluoromethylbenzyl)imidazole-4,5-dicarboxamide and 1-(3,5-dichloro-α-methoxybenzyl)-N,N'-dimethylimidazole-4,5-dicarboxamide, and more especially N,N'-dimethyl- 1-(3,4-dichloro-α-methoxybenzyl)imidazole-4,5-dicarboxamide, N,N'-dimethyl-1-(3,4-dichloro-α-ethoxybenzyl)imidazole-4,5-dicarboxamide, N,N'-dimethyl-1-(α-methoxy-4-trifluoromethylbenzyl)imidazole-4,5-dicarboxamide and 1-(3,4-dibromo-α-methoxybenzyl)-N,N'-dimethylimidazole-4,5-dicarboxamide, may be used to control selectively the growth of annual broad leaf weeds, for example to control the growth of those annual broad leaf weed species hereinbefore mentioned, by post-emergence application in a non-directional fashion, e.g. by non-directional spraying, to an area used for growing crops of cereals, cotton or soya bean after emergence of both the crop and weeds.

For this purpose, i.e. the selective control of annula broad leaf weeds by post-emergence application to an area used for growing crops of cereals, cotton or soya bean, application rates between 0.25 kg and 8.0 kg of active material per hectare are particularly suitable. More especially (±)-N,N'-dimethyl-1-(3,4-dichloro-α-methoxybenzyl)imidazole-4,5-dicarboxamide at rates of 0.5 to 4 kg/ha gives excellent control of broad leaf weeds by post-emergence application in cotton.

When used to control the growth of weeds by pre-emergence application, the compounds of general formula I may be incorporated into the soil in which the weeds are expected to emerge. It will be appreciated that when the compounds of general formula I are used to control the growth of weeds by post-emergence application, i.e. by application to the aerial or exposed portions of emerged weeds, the compounds of general formula I will also normally come into contact with the soil and may also then exercise a pre-emergence control on later-germinating weeds in the soil.

Where especially prolonged weed control is required, the application of the compounds of general formula I may be repeated if required.

According to a feature of the present invention, the compounds of general formula I wherein $R^1$, $R^2$, $R^3$ and $R^4$ are as hereinbefore defined are prepared by the following processes:

Process 1

The reaction of a compound of the general formula:

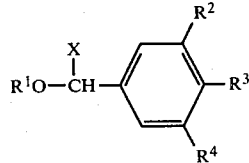

II (wherein X represents a halogen, preferably chlorine or bromine, atom, and $R^1$, $R^2$, $R^3$ and $R^4$ are as hereinbefore defined) with an alkali metal, preferably sodium, salt of imidazole-N,N'-dimethyl-4,5-dicarboxamide of the formula:

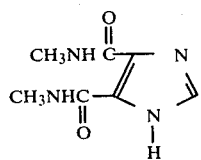

III

The reaction may be effected in the presence of an inert organic solvent, such as dimethylformamide or t-butanol, at a temperature between ambient temperature and 150° C., and preferably at a temperature between 50° C. and 110° C.

Process 2

The reaction of a compound of the general formula:

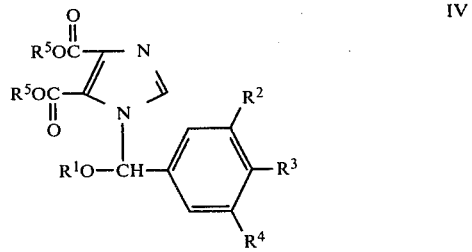

IV (wherein $R^1$, $R^2$, $R^3$ and $R^4$ are as hereinbefore defined, and $R^5$ represents a straight- or branched-chain alkyl group containing from 1 to 6 carbon atoms) with methylamine in the presence of an inert organic solvent, such as toluene or ethanol, at a temperature between 0° and 100° C.

The compounds of general formula II may be prepared by known methods, for example by the procedure described in British patent specification No. 1,230,347.

The compound of formula III may be prepared by the reaction of the compound of the formula:

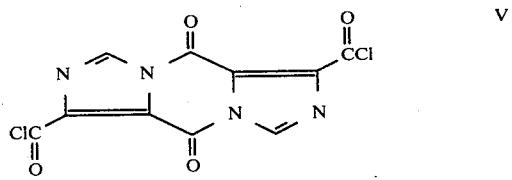

V with methylamine in the presence of an acid-binding agent, which is preferably an excess of methylamine, and an inert organic solvent, e.g. toluene, at a temperature between 0° and 30° C., and preferably at ambient temperature.

Alternatively, the compounds of formula III may be prepared by the reaction of a compound of the general formula:

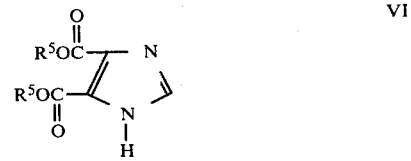

VI (wherein $R^5$ is as hereinbefore defined) with methylamine. The reaction may be effected in a manner similar to that hereinbefore described in Process 2.

The compound of formula V may be prepared by the reaction of imidazole-4,5-dicarboxylic acid of formula:

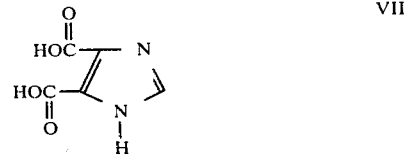

VII with thionyl chloride. The reaction may be effected optionally in the presence of an inert organic solvent, optionally in the presence of a catalytic amount of dimethylformamide or pyridine, at the reflux temperature of the reaction mixture.

The compounds of general formula VI may be prepared by the reaction of the compound of formula VII with an alkanol containing from 1 to 6 carbon atoms, e.g. ethanol, in the presence of an acid catalyst, e.g. hydrogen chloride. The reaction may conveniently be effected by bubbling gaseous hydrogen chloride through an alkanolic, e.g. ethanolic, solution of the compound of formula VII at the reflux temperature of the reaction mixture.

The compounds of general formula IV may be prepared by the reaction of a compound of general formula II with an alkali metal, preferably sodium, salt of a compound of general formula VI. The reaction may be effected in a manner similar to that hereinbefore described in Process 1.

The alkali metal salts of compounds of formula III and of general formula VI may optionally be prepared in situ, by the application or adaptation of known methods, for example the sodium salts thereof may be prepared by the reaction of compounds of formula III and VI with sodium hydride in the presence of dimethylformamide.

The potassium salts of compounds of general formula VI may be prepared by the reaction of a compound of general formula VI with potassium t-butoxide in the presence of dimethylformamide.

By the term "known methods" as used in the present specification is meant methods heretofore used or described in the chemical literature.

The following Example illustrates the preparation of the compounds of the present invention.

EXAMPLE 1

Sodium hydride (9.0 g) was added to a stirred suspension of imidazole-N,N'-dimethyl-4,5-dicarboxamide [described by Vinogradova and Khromov-Borisov, Zhur. Obschii. Khim, 31, 1466 (1961)] in dry dimethylformamide (350 ml). The temperature of the mixture rose to 50° C. and was then maintained at 40°–50° C. for 2.5 hours until all the solid material had dissolved. The solution thus obtained was cooled to 15° C. and maintained at this temperature during the addition, over 0.5 hours, of 3,4-dichloro-α-methoxybenzyl chloride (84.6 g). The mixture was then stirred for 2.5 hours, maintained at laboratory temperature (about 25° C.) for a further 16 hours and then heated, with stirring, for a further 2 hours at 50°–60° C. The solution thus obtained was filtered and the solid residue was washed with dry dimethylformamide. The combined filtrate and washings were added to water (2.5 liters) and the oil which precipitated was extracted with diethyl ether (3×1.2 liters). The combined ethereal extracts were washed with water (8×50 ml). The combined strongly alkaline aqueous liquors and washings were acidified to pH 3-4 with concentrated hydrochloric acid and the diethyl ether which separated from them was washed with water (4×50 ml) and combined with ethereal extract previously obtained. The combined ethereal solutions were dried over anhydrous sodium sulphate and evaporated to give a crude product (129 g) which was purified by treatment with hot hexane (1.4 liters) and diethyl ether (350 ml), treatment with charcoal and filtration, after which the product slowly crystallised and was separated to give (+)-N,N'-dimethyl-1-(3,4-dichloro-α-methoxybenzyl)-imidazole-4,5-dicarboxamide (76 g), m.p. 112°–114° C., as a white microcrystalline solid.

By proceeding in a similar manner, but replacing the 3,4-dichloro-α-methoxybenzyl chloride by the appropriately substituted α-alkoxybenzyl chlorides, there were prepared:

(+)-N,N'-dimethyl-1-(3,4-dichloro-α-ethoxybenzyl)imidazole-4,5-dicarboxamide, m.p. 115°–117° C. (after crystallisation from hexane), from 3,4-dichloro-α-ethoxybenzyl chloride;

(+)-1-(4-chloro-α-methoxybenzyl)-N,N'-dimethylimidazole-4,5-dicarboxamide, m.p. 93°–94° C. (after crystallisation from petroleum ether b.p. 60°–80° C.), from 4-chloro-α-methoxybenzyl chloride;

(+)-1-(3-chloro-α-methoxybenzyl)-N,N'-dimethylimidazole-4,5-dicarboxamide, m.p. 120° C. (after crystallisation from a mixture of methanol and petroleum ether b.p. 60°–80° C.), from 3-chloro-α-methoxybenzyl chloride.

(+)-N,N'-dimethyl-1-(α-methoxy-4-trifluoromethylbenzyl)-imidazole-4,5-dicarboxamide, m.p. 78° C. (after crystallisation from petroleum ether b.p. 60°–80° C.), from α-methoxy-4-trifluoromethylbenzyl chloride;

(+)-1-(3,4-dibromo-α-methoxybenzyl)-N,N'-dimethylimidazole-4,5-dicarboxamide, m.p. 113.5°–114° C. (after crystallisation from petroleum ether b.p. 60°–80° C.), from 3,4-dibromo-α-methoxybenzyl chloride;

(+)-N,N'-dimethyl-1-(α-methoxy-3-trifluoromethylbenzyl)imidazole-4,5-dicarboxamide, m.p. 75°–77° C. (after crystallisation from petroleum ether b.p. 60°–80° C.), from α-methoxy-3-trifluoromethylbenzyl chloride;

(+)-1-(3,5-dichloro-α-methoxybenzyl)-N,N'-dimethylimidazole-4,5-dicarboxamide, m.p. 155°–156° C. (after crystallisation from a mixture of toluene and petroleum ether b.p. 60°–80° C.), from 3,5-dichloro-α-methoxybenzyl chloride.

The α-alkoxybenzyl chlorides used as starting materials in the above preparations were prepared according to the procedure described in British patent specification No. 1,230,347, by the following method:

A mixture of acetyl chloride (77 g) and thionyl chloride (0.8 ml) was added, with stirring, to 3,4-dichlorobenzaldehyde dimethyl acetal (110 g). The mixture was kept at laboratory temperature (about 27° C.) for 22 hours and then evaporated at 30° C. under reduced pressure (0.15 mm Hg) for about 4 hours until constant in weight. 3,4-Dichloro-α-methoxybenzyl chloride (112 g) was thus obtained as an oil, which was used without further purification as a starting material in the above preparations.

By proceeding in a similar manner, but replacing the 3,4-dichlorobenzaldehyde dimethyl acetal by the appropriately substituted benzaldehyde dialkyl acetals, there were prepared:

3,4-dichloro-α-ethoxybenzyl chloride, as a clear, mobile oil, from 3,4-dichlorobenzaldehyde diethyl acetal;

4-chloro-α-methoxybenzyl chloride, as a clear, mobile oil, from 4-chlorobenzaldehyde dimethyl acetal;

3-chloro-α-methoxybenzyl chloride as a clear, mobile oil, from 3-chlorobenzaldehyde dimethyl acetal;

α-methoxy-4-trifluoromethylbenzyl chloride, as a clear mobile oil, from 4-trifluoromethylbenzaldehyde dimethyl acetal;

3,4-dibromo-α-methoxybenzyl chloride, as a clear, mobile oil from 3,4-dibromobenzaldehyde dimethyl acetal;

α-methoxy-3-trifluoromethylbenzyl chloride, as a clear, mobile oil, from 3-trifluoromethylbenzaldehyde dimethyl acetal;

3,5-dichloro-α-methoxybenzyl chloride, as a clear, mobile oil, from 3,5-dichlorobenzaldehyde dimethyl acetal.

The benzaldehyde acetals used as starting materials in the above preparations were prepared according to the procedure described in British patent specification No. 1,230,347 by the following method:

Concentrated hydrochloric acid (1.0 ml) was added to a stirred suspension of 3,4-dichlorobenzaldehyde (140 g) in a mixture of trimethyl orthoformate (94 g) and dry methanol (400 ml). After stirring for 24 hours at laboratory temperature (about 25° C.), the reaction solution was adjusted to pH 7–8 by the addition of a solution of sodium methoxide in methanol and concentrated on a rotary evaporator. The residual oil was then dissolved in diethyl ether (600 ml). The ethereal solution was washed with water until the washings were neutral and then dried over anhydrous sodium sulphate, filtered and distilled to give 3,4-dichlorobenzaldehyde dimethyl acetal (157.5 g). b.p. 137°–140° C./25 mm Hg, as a clear mobile oil.

By proceeding in a similar manner, but replacing the 3,4-dichlorobenzaldehyde by the appropriate substituted benzaldehyde and, where indicated, the trimethyl orthoformate by triethyl orthoformate and the methanol by ethanol, there were prepared:

3,4-dichlorobenzaldehyde diethyl acetal, b.p. 137°–138° C./15 mm Hg, from 3,4-dichlorobenzaldehyde, triethyl otthoformate and ethanol;

4-chlorobenzaldehyde dimethyl acetal, b.p. 112° C./20 mm Hg, from 4-chlorobenzaldehyde;

3-chlorobenzaldehyde dimethyl acetal, b.p. 98°–100° C./20 mm Hg, from 3-chlorobenzaldehyde;

4-trifluoromethylbenzaldehyde dimethyl acetal, b.p. 80°–83° C./17 mm Hg, from 4-trifluoromethylbenzaldehyde;

3,4-dibromobenzaldehyde dimethyl acetal, b.p. 150° C./20 mm Hg, from 3,4-dibromobenzaldehyde;

3-trifluoromethylbenzaldehyde dimethyl acetal, b.p. 88°–90° C./15 mm Hg, from 3-trifluoromethylbenzaldehyde;

3,5-dichlorobenzaldehyde dimethyl acetal, b.p. 118°–123° C./17 mm Hg, from 3,5-dichlorobenzaldehyde.

According to a further feature of the present invention, there are provided compositions suitable for herbicidal use comprising one or more of the imidazole derivatives of general formula I in association with, and preferably homogeneously dispersed in, one or more compatible herbicidally-acceptable diluents or carriers (i.e. diluents or carriers of the type generally accepted in the art as being suitable for use in herbicidal compositions and which are compatible with compounds of general formula I). The term "homogeneously dispersed" is used to include compositions in which the compounds of general formula I are dissolved in the other components. The term "herbicidal compositions" is used in a broad sense to include not only compositions which are ready for use as herbicides but also concentrates which must be diluted before use. Preferably, the compositions contain from 0.05 to 90% by weight of one or more compounds of general formula I.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid ester of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the compounds of general formula I with solid diluents or by impregnating the solid diluents or carriers with solutions of the compounds of general formula I in volatile solvents, evaporating the solvents and, if necessary, grinding the products so as to obtain powders. Granular formulations may be prepared by absorbing the compounds of general formula I (dissolved in volatile solvents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers. The addition of an organic base, for example a tertiary amine preferably triethanolamine (0.1–10% w/v), to maintain alkaline conditions in liquid formulations, is beneficial for long term stability. Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the compound of general formula I may be used in the form of self-emulsifying concentrates containing the active substances dissolved in the emulsifying agents or in solvents containing emulsifying agents compatible with the active substances, the simple addition of water to such concentrates producing compositions ready for use.

Herbicidal compositions according to the present invention may also contain, if desired, conventional adjuvants such as adhesives, colouring agents and corrosion inhibitors. These adjuvants may also serve as carriers or diluents.

Herbicidal compositions according to the present invention may also comprise the compounds of general formula I in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, e.g. bentazone (3-isopropyl-2,1,3-benzothiadiazin-4-one-2,2-dioxide), chloroxuron [N'-4-(4-chlorophenoxy)phenyl-N,N-dimethylurea], fluometuron [N'-(3-trifluoromethylphenyl)-N,N-dimethylurea], diuron [N'-(3,4-dichlorophenyl)-N,N-dimethylurea], metribuzin [4-amino-6-t-butyl-3-methylthio-1,2,4-triazin-5(4H)-one], MSMA (monosodium methylarsonate), alloxydimedon sodium {2-[1-(N-allyloxyamino)butylidene]-5,5-dimethyl-4-methoxycarbonylcyclohexane-1,3-dione}, mefluidide (5-trifluoromethylsulphonylamino-2,4-acetoxylidide), diclofop-methyl {methyl (±)-2-[4-(2,4-dichlorophenoxy)-phenoxy]propionate} and clofop-isobutyl {isobutyl (±)-2-[4-(4-chlorophenoxy)phenoxy]propionate} and insecticides, e.g. dimethonate (O,O-dimethyl S-methylcarbamoylmethylphosphorodithioate), monocrotophos [(E)dimethyl 1-methyl-2-methylcarbamoylvinylphosphate], organochlorine compounds, e.g. endosulphan {6,7,8,9,10,10-hexachloro-1,5,5a,6,9,9a-hexahydro-6,9-methano-2,4,3-benzo[e]dioxathiepin-3-oxide}, and carbamates, e.g. carbaryl (1-naphthyl methylcarbamate). Other biologically active materials which may be included in, or used in conjunction with, the herbicidal compositions of the present invention include fertilizers e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilised in the form of conventional derivatives, for example alkali metal and amine salts and esters.

According to a further feature of the present invention there is provided an article of manufacture comprising at least one of the imidazole derivatives of general formula I or, as is preferred, a herbicidal composition as hereinbefore described, and preferably a herbicidal concentrate which must be diluted before use, comprising at least one of the imidazole derivatives of general formula I within a container for the aforesaid derivative or derivatives of general formula I, or a said herbicidal composition, and instructions physically associated with the aforesaid container setting out the manner in which the aforesaid derivative or derivatives of general formula I or herbicidal composition contained therein is to be used to control the growth of weeds. The containers will normally be of the types conventionally used for the storage of chemical substances which are solids at normal ambient temperatures and herbicidal compositions particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the imidazole derivatives or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 0.25 kg and 20 kg of active material per hectare in the manner and for the purposes hereinbefore described.

The following Examples illustrate herbicidal compositions according to the present invention.

EXAMPLE 2

An aqueous suspension concentrate is formed from:
(±)-N,N'-dimethyl-1-(3,4-dichloro-α-methoxybenzyl)imidazole-4,5-dicarboxamide: 40% w/v
Ethylan BCP (a nonylphenol-ethylene oxide condensation product containing 9 moles of ethylene oxide per mole of phenol): 5% w/v
distilled water: 100% by volume
by intimately mixing the ingredients and grinding in a ball mill for 24 hours. The concentrate thus obtained may be dispersed in water and applied at a rate of 2.0 kg of imidazole derivative in 200 liters of spray fluid per hectare to a crop growing area planted with soya bean to control the growth of broad-leaf weeds, for example *Abutilon theophrasti, Xanthium strumarium* and *Ipomoea purpurea* by post-emergence application after emergence of crop and weeds.

The (±)-N,N'-dimethyl-1-(3,4-dichloro-α-methoxybenzyl)imidazole-4,5-dicarboxamide may, if desired, be replaced in the above aqueous suspension concentrate by any other compound of general formula I.

EXAMPLE 3

A wettable powder concentrate is formed from:
(±)-N,N'-dimethyl-1-(3,4-dichloro-α-methoxybenzyl)imidazole-4,5-dicarboxamide: 50% w/w
Ethylan BCP: 2.5% w/w
Clarcelflo SAS 132 (synthetic magnesium silicate carrier): 47.5% w/w
by dissolving the imidazole and Ethylan BCP in the minimum volume of acetone and adding the solution to the Clarcelflo in a blender. After the acetone has evaporated, the product is ground in a hammer mill to give a wettable powder which may be dispersed in water and applied at a rate of 3 kg of imidazole derivative in 400 liters of spray fluid per hectare to a crop growing area sown with cotton to control the growth of broad-leaf weeds e.g. *Sida spinosa, Abutilon theophrasti, Anoda cristata* and *Amaranthus retroflexus* by postemergence application after emergence of the crop and weeds.

The (±)-N,N'-dimethyl-1-(3,4-dichloro-α-methoxybenzyl)imidazole-4,5-dicarboxamide may, if desired, be replaced in the above wettable powder by any other compound of general formula I.

EXAMPLE 4

An emulsifiable concentrate is formed from:
(±)-N,N'-dimethyl-1-(3,4-dichloro-α-methoxybenzyl)imidazole-4,5-dicarboxamide: 20% w/v Duoterics MB1/MB2 (an anionic emulsifier blend containing calcium alkyl sulphonate and alkyl phenol ethylene oxide condensates): 10% w/v triethanolamine: 1% w/v a 1:1 by volume mixture of cyclohexanone and Aromasol "H" (an aromatic solvent consisting predominantly of isomeric trimethylbenzenes) to: 100% by volume by dissolving the imidazole derivative and the Duoterics MB1/MB2 and triethanolamine in a portion of the 1:1 cyclohexanone and Aromasol "H" mixture, and adding, with stirring, the remainder of the cyclohexanone-Aromasol "H" mixture. The emulsifiable concentrate thus obtained may be diluted with water and applied at a rate of 1.0 kg of imidazole derivative in 200 liters of spray fluid per hectare to a crop area planted with cotton to control the growth of *Amaranthus retroflexus, Acanthospermum hispidum, Abutilon theophrasti, Bidens pilosa, Sida spinosa, Xanthium strumarium, Ipomoea purpurea* and Physalis sp. by post-emergence application after the emergence of both crop and weeds.

The (±)-N,N'-dimethyl-1-(3,4-dichloro-α-methoxybenzyl)imidazole-4,5-dicarboxamide may, if desired, be replaced in the above emulsifiable concentrate by any other compound of general formula I.

We claim:

1. An imidazole derivative of the formula:

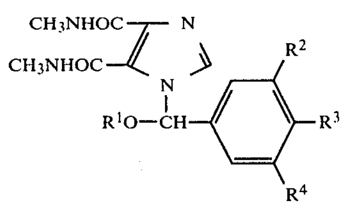

I wherein $R^1$ represents a methyl or ethyl group, $R^2$, $R^3$ and $R^4$, which may be the same or different, each represent hydrogen or halogen or an alkyl or alkoxy group which may optionally be substituted by one or more fluorine atoms, and $R^2$, $R^3$ and $R^4$ do not all represent hydrogen.

2. An imidazole derivative according to claim 1 wherein one of the symbols $R^2$, $R^3$ and $R^4$ represents hydrogen and the other two symbols and $R^1$ are as defined in claim 1.

3. An imidazole derivative according to claim 1 wherein $R^1$ is as defined in claim 1, $R^2$ and $R^3$, which may be the same or different, each represent hydrogen or halogen or an alkyl group which may optionally be substituted by one or more fluorine atoms and $R^2$ and $R^3$ do not both represent hydrogen, and $R^4$ represents hydrogen or halogen.

4. An imidazole derivative according to claim 1 wherein $R^1$ is as defined in claim 1, $R^2$ and $R^3$ each represent halogen or $R^2$ represents hydrogen and $R^3$ represents halogen or an alkyl group which may optionally be substituted by one or more fluorine atoms, and $R^4$ represents hydrogen.

5. An imidazole derivative according to claim 1 wherein $R^1$ represents a methyl group.

6. An imidazole derivative according to claim 1 wherein, within the definition of $R^2$, $R^3$ and $R^4$, the or each halogen is chlorine or bromine and the or each alkyl or alkoxy group which may optionally be substituted by one or more fluorine atoms is a trifluoromethyl, trifluoromethoxy or 1,1,2,2-tetrafluoroethoxy group.

7. An imidazole derivative according to claim 6 wherein the or each alkyl or alkoxy group which may optionally be substituted by one or more fluorine atoms is a trifluoromethyl group.

8. An imidazole derivative according to claim 1 which is N,N'-dimethyl-1-(3,4-dichloro-α-methoxybenzyl)imidazole-4,5-dicarboxamide.

9. An imidazole derivative according to claim 1 which is N,N'-dimethyl-1-(3,4-dichloro-α-ethoxybenzyl)imidazole-4,5-dicarboxamide.

10. An imidazole derivative according to claim 1 which is N,N'-dimethyl-1-(α-methoxy-4-trifluoromethylbenzyl)imidazole-4,5-dicarboxamide.

11. An imidazole derivative according to claim 1 which is 1-(3,4-dibromo-α-methoxybenzyl)-N,N'-dimethylimidazole-4,5-dicarboxamide.

12. An imidazole derivative according to claim 1 which is 1-(4-chloro-α-methoxybenzyl)-N,N'-dimethylimidazole-4,5-dicarboxamide.

13. An imidazole derivative according to claim 1 which is 1-(3-chloro-α-methoxybenzyl)-N,N'-dimethylimidazole-4,5 -dicarboxamide.

14. An imidazole derivative according to claim 1 which is N,N'-dimethyl-1-(α-methoxy-3-trifluoromethylbenzyl)imidazole-4,5-dicarboxamide.

15. An imidazole derivative according to claim 1 which is 1-(3,5-dichloro-α-methoxybenzyl)-N,N'-dimethylimidazole-4,5-dicarboxamide.

16. A herbicidal composition which comprises at least one imidazole derivative as claimed in claim 1 in association with one or more compatible herbicidally acceptable diluents or carriers, the amount of imidazole derivative in the composition being 0.05 to 90% by weight.

17. A herbicidal composition according to claim 16 wherein the imidazole derivative incorporated in the composition is N,N'-dimethyl-1-(3,4-dichloro-α-methoxybenzyl)imidazole-4,5-dicarboxamide, N,N'-dimethyl-1-(3,4-dichloro-α-ethoxybenzyl-)imidazole-4,5-dicarboxamide, N,N'-dimethyl-1-(α-methoxy-4-trifluoromethylbenzyl)imidazole-4,5-dicarboxamide, 1-(3,4-dibromo-α-methoxybenzyl)-N,N'-dimethylimidazole-4,5-dicarboxamide, 1-(4-chloro-α-methoxybenzyl)-N,N'-dimethylimidazole-4,5-dicarboxamide, 1-(3-chloro-α-methoxybenzyl)-N,N'-dimethylimidazole-4,5-dicarboxamide, N,N'-dimethyl-1-(α-methoxy-3-trifluoromethylbenzyl)imidazole-4,5-dicarboxamide or 1-(3,5-dichloro-α-methoxybenzyl)-N,N'-dimethylimidazole-4,5-dicarboxamide.

18. A method of controlling the growth of weeds at a locus which comprises applying to the locus a herbicidal composition containing a herbicidally effective amount of an imidazole derivative as claimed in claim 1.

19. A method according to claim 18 in which the weeds are annual broad-leafed weeds and the herbicidal composition is applied post-emergence.

20. A method according to claim 18 in which weeds controlled by application of the herbicidal composition are one or more of *Abutilon theophrasti, Amsinckia intermedia, Anthemis arvensis,* Amaranthus spp., *Anoda cristata,* Acanthospermum spp., *Bidens pilosa,* Chenopodium spp., *Chrysanthemum segetum, Datura stramonium, Descurainea sophia, Emex australis, Galeopsis tet-* rahit, Ipomoea spp., Lamium spp., *Merremia aegyptea, Papaver rhoeas,* Physalis spp., *Sida spinosa, Sida rhombifolia,* Sinapis spp., *Stellaria media,* Solanum spp., *Urtica urens,* Veronica spp., and *Xanthium strumarium.*

21. A method according to claim 18 in which the herbicidal composition is applied to a crop-growing area at a rate sufficient to control the growth of weeds without causing substantial permanent damage to the crop.

22. A method according to claim 18 in which the imidazole derivative is applied at a rate between 0.25 kg and 20 kg per hectare.

23. A method according to claim 18 for the selective control of the growth of weeds in an area used, or to be used, for growing crops.

24. A method according to claim 23 in which the imidazole derivative is applied at a rate between 0.25 kg and 8.0 kg per hectare.

25. A method according to claim 23 in which the crop is a graminaceous crop, soya beans, field or dwarf beans, peas, sugar beet, fodder beet or red beet, cotton, peanuts, potatoes, flax, onions, carrots, herbage seed crops, oilseed rape or pasture.

26. A method according to claim 25 in which the graminaceous crop is wheat, barley, oats, rye, maize, rice or sorghum.

27. A method according to claim 18 in which the herbicidal composition contains as active material 1-(4-chloro-α-methoxybenzyl)-N,N'-dimethylimidazole-4,5-dicarboxamide, 1-(3-chloro-α-methoxybenzyl)-N,N'-dimethylimidazole-4,5-dicarboxamide, N,N'-dimethyl-1-(α-methoxy-3-trifluoromethylbenzyl)imidazole-4,5-dicarboxamide and 1-(3,5-dichloro-α-methoxybenzyl)-N,N'-dimethylimidazole-4,5-dicarboxamide, N,N'-dimethyl-1-(3,4-dichloro-α-methoxybenzyl)imidazole-4,5-dicarboxamide, N,N'-dimethyl-1-(3,4-dichloro-α-ethoxybenzyl)imidazole-4,5-dicarboxamide, N,N'-dimethyl-1-(α-methoxy-4-trifluoromethylbenzyl)imidazole-4,5 -dicarboxamide or 1-(3,4-dibromo-α-methoxybenzyl)-N,N'-dimethylimidazole-4,5-dicarboxamide.

28. A method according to claim 27 in which the weeds are controlled by post-emergence application of the herbicidal composition in a non-directional fashion to an area used for growing crops of cereals, cotton or soya bean after emergence of the crop and weeds.

29. A method according to claim 27 in which the imidazole derivative is applied at a rate between 0.25 kg and 8.0 kg per hectare.

30. A method according to claim 28 in which (±)-N,N'-dimethyl-1-(3,4-dichloro-α-methoxybenzyl)imidazole-4,5-dicarboxamide is applied at a rate of 0.5 to 4 kg/ha to control broad-leaf weeds in a crop of cotton.

* * * * *